(12) United States Patent
Ishikawa et al.

(10) Patent No.: US 6,527,694 B1
(45) Date of Patent: Mar. 4, 2003

(54) AIR-COOLING DEVICE FOR COIL FOR URINARY INCONTINENCE TREATMENT

(75) Inventors: Norio Ishikawa, Tokyo (JP); Shin Suda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/676,665

(22) Filed: Oct. 2, 2000

(30) Foreign Application Priority Data

Sep. 30, 1999 (JP) .......................................... 11-278360

(51) Int. Cl.[7] .............................. A61B 17/52; A61N 2/00
(52) U.S. Cl. ........................................................ 600/9
(58) Field of Search ................................. 600/9, 10, 11, 600/12, 13, 14, 15; 607/61; 415/117, 213.1; 165/80.3; 361/697

(56) References Cited

U.S. PATENT DOCUMENTS

| | | | |
|---|---|---|---|
| 5,116,304 A | | 5/1992 | Cadwell |
| 5,615,998 A | * | 4/1997 | Kodama et al. ............. 415/177 |
| 5,725,471 A | | 3/1998 | Davey et al. |
| 5,984,854 A | | 11/1999 | Ishikawa et al. ................ 600/9 |
| 5,991,665 A | * | 11/1999 | Wang et al. .................... 607/61 |
| 6,007,476 A | * | 12/1999 | Wascher et al. ................ 600/9 |
| 6,083,149 A | * | 7/2000 | Wascher et al. ................ 600/9 |
| 6,086,525 A | | 7/2000 | Davey et al. |
| 6,179,770 B1 | | 1/2001 | Mould |

FOREIGN PATENT DOCUMENTS

| | | |
|---|---|---|
| EP | 0 850 665 A2 | 7/1998 |
| GB | 2 201 298 A | 8/1988 |
| GB | 2 336 554 A | 10/1999 |
| JP | 63-274121 | 11/1988 |
| JP | 9-276418 | 10/1997 ............ A61N/1/40 |
| JP | 2743245 | 2/1998 ............ A61N/2/08 |
| JP | 2588120 | 10/1998 ............ A61N/2/08 |
| WO | WO 98/34243 | 8/1998 |
| WO | WO 99/33516 | 7/1999 |

OTHER PUBLICATIONS

Japanese Patent Abstract 07116273 May 9, 1995.

* cited by examiner

Primary Examiner—Max Hindenburg
Assistant Examiner—Brian Szmal
(74) Attorney, Agent, or Firm—Sughrue Mion, PLLC

(57) ABSTRACT

A core (20) is housed in a box (10) in which a box upper board (11) is electrically insulative and nonmagnetic. The core has front and rear side legs (23) directed toward the box upper board (11). A coil (26) is wound around the core (20). An air way (12a) is formed in a box bottom board (12). A blower (16) is attached to the air way. Other air ways which cooperate with the air way (12a) to form air pathways passing over the coil (26) are formed in box side boards (13). Pulse current or alternating current is supplied to the coil (26) to generate magnetic fluxes toward a region from a front of the urethral orifice to a rear of the anus, so that urinary incontinence is treated by eddy currents induced in the living body.

39 Claims, 10 Drawing Sheets

AIR-COOLING DEVICE FOR COIL FOR URINARY INCONTINENCE TREATMENT

BACKGROUND OF INVENTION

1. Field of Invention

The present invention relates to an air-cooling device for a coil for urinary incontinence treatment, used for air-cooling a coil to which pulse current or alternating current is supplied to generate magnetic fluxes toward a range from a front of the urethral orifice to a rear of the anus, to induce eddy currents in a living body, thereby treating urinary incontinence.

2. Related Art

A proposed urinary incontinence treatment apparatus is described in U.S. Pat. No. 5,984,854. In the proposed apparatus, a magnetic stimulation coil which is disposed on a coil mount to be placed in a room, and which generates repetitive pulse-like magnetic fluxes is set in a portion in a range from the waist of a patient to a lower limb region, and the pelvic floor muscles, pudendal nerves, and the like are stimulated by eddy currents due to magnetic fluxes penetrating the body. In this case, in order to generate a sufficient amount of magnetic fluxes, large current must be supplied to the coil. Therefore, also a cooling device has been proposed in the publication. The air-cooling device is used for circulating water through the coil in order to prevent the patient from suffering low- or high-temperature burn due to heat generation of the coil, and to prevent the efficiency from being lowered by the direct current resistance of the coil which is increased as a result of temperature rise. In the publication, also a technique in which the coil may be cooled by a fan or a Peltier element is suggested.

However, since large current is needed for the device, heat generation of the coil is also large. In order to reduce the temperature rise of the coil by heat generation and also in the case of using core(s), the heat generation of the core(s) by eddy currents, a device in which water is circulated or a Peltier element is used has problems to be solved, namely, a bulky structure, a large power consumption, and a high cost. Furthermore, it is difficult to attain a sufficient cooling effect by simply attaching a fan in the side of or in the front (rear) side of a cored-coil and blowing air in one direction with the fan.

In view of these problems, it is an object of the invention to provide an air-cooling device for a coil for urinary incontinence treatment which can be efficiently force-cooled by using a blower.

SUMMARY OF INVENTION

In order to attain the object, according to a first aspect of the invention, the invention is an air-cooling device for a coil for urinary incontinence treatment, used for air-cooling a coil to which pulse current or alternating current is supplied to generate magnetic fluxes toward a range from a front of an urethral orifice to a rear of an anus, to induce eddy currents in a living body, thereby treating urinary incontinence, and characterized in that a coil is housed in a box having an upper board which is electrically insulative and nonmagnetic, the coil being wound along the box upper board, an air way is formed in a bottom board of the box, a blower is attached to the air way, and a second air way is formed in a region of a side board of the box, the region being opposed to the coil.

Since the coil is wound along the box upper board, magnetic fluxes can be generated in an upward direction from the box upper board. The sitting patient is isolated from the coil and the generated magnetic fluxes are not confined into the box, because the box upper board is electrically insulative and nonmagnetic. Air pathways which pass over the vicinity of the coil are formed between the air ways of the box bottom board and the box side boards as a result of suction and discharge of the blower.

According to a second aspect of the present invention, in order to efficiently air-cool the coil in the case where the coil is a solenoid coil directed toward the box bottom board, the position of said second air way is equal to or higher in height than that of said coil.

According to a third aspect of the invention, in order to efficiently concentrate magnetic fluxes when the box upper board is formed to have a concave surface so as to correspond to the portion on which the patient is to sit, the box upper board is formed to have a concave surface, and an upper face of the coil is inclined along the box upper board.

According to a fourth aspect of the invention, in order to attain the object in the case where the coil is provided with a core, a core which has front and rear side legs and around which a coil is wound is housed in a box having an upper board which is electrically insulative and nonmagnetic, the legs elongating toward the box upper board, an air way is formed in a bottom board of the box, a blower is attached to the air way, and a second air way is formed in at least one of box side boards, the second air way cooperating with the first air way to form an air pathway through the coil and the core.

Magnetic fluxes can be upward generated between the end faces of the front and rear side legs which are directed toward the box upper board. Air pathways which pass over the vicinities of the coil and the center core are formed between the air ways of the box bottom board and the box side board(s) as a result of suction and discharge of the blower. In view of efficiency, preferably, the air way of the box side board is set to be in a region opposed to the coil, or, in the case where the coil is wound around a bottom portion of the core, in a region above the coil and opposed to an upper portion of the core. In the case of a cored coil, magnetic fluxes are more concentrated even at the same coil current compared to an air-core coil, so that stimulation can be efficiently performed.

In the case of an E-type core, according to a fifth aspect of the invention, the core has an E-like shape in which a center leg is formed between the front and rear side legs, the coil being wound around the center leg, and the second air way of the box side board is formed in a region opposed to the coil. Magnetic fluxes are generated between the center leg and the front and rear side legs, and can be concentrated particularly to the center leg. According to a seventh aspect of the invention, in order to concentrate magnetic fluxes more efficiently in the case of a cored coil, the front and rear side legs protrude from the box to a level which is higher than the box upper board.

According to an eighth aspect of the invention, in order to perform forced cooling more efficiently, a conductive member constituting the coil is wound with forming a gap over a whole periphery of the coil. In the case of a cored coil, a spacer may be interposed between the coil and the core. According to a ninth aspect of the invention, with the same object, heat radiating fins are attached to the coil in radial directions. According to a tenth aspect of the invention, in the case of a cored coil, heat radiating fins are attached to the core in radial directions.

When the air-cooling device is configured as an urinary incontinence treatment apparatus, according to an eleventh aspect of the invention, legs are downward disposed on the bottom board of the box, the legs being used for placing the box under a state where the blower is separated from a floor to enable the box itself to function as a chair.

In order to configure an urinary incontinence treatment apparatus which is incorporated into a chair, and which has a high air cooling efficiency, according to a twelfth aspect of the invention, the box is mounted in the seat portion which is attached between side portions each constituting a leg and an armrest of the chair, ducts are respectively formed between the box side boards and the side portions opposed to the box side boards, the blower is placed to the bottom board of the ducts, cutout portions communicating with the ducts are formed in side end portions of the-seat portion, respectively, and ventilation cutout portions are formed in intermediate regions in anteroposterior directions of the side portions and in side areas of the blower.

According to a thirteenth aspect of the invention, in order to further enhance the air cooling function, the coil is configured by a pipe-shaped conductor member, ends of the conductor member are connected to side faces of the box, one of the ends is opened in air, and a blower is attached to another one of the ends.

BRIEF DESCRIPTION OF PREFERRED EMBODIMENTS

FIG. 6A is a section view of the device, and FIG. 6B is a section view of a modification of the device;

FIG. 9A is a section view of the device, and FIG. 9B is a perspective view of the device;

FIG. 11A is a perspective view of the device, and FIG. 11B is a rear view of the device.

DETAILED DESCRIPTION OF PREFERRED EMBODIMENTS

Figure 2:
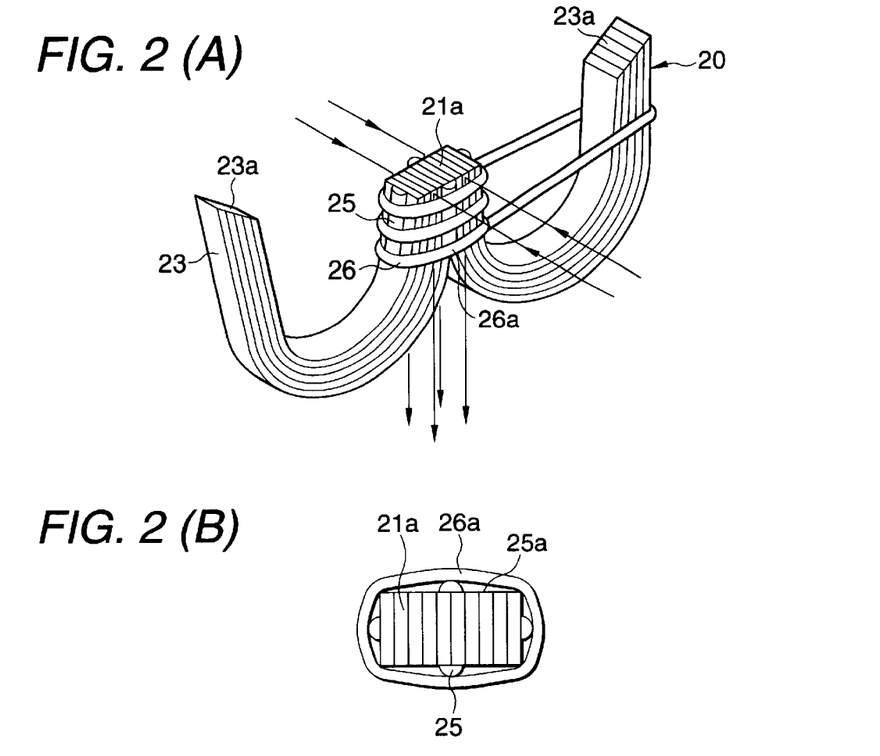
FIG. 2(a) is a perspective view of a cored coil housed in a box of the air-cooling device.
FIG. 2(b) is a plan view of the cored coil housed in a box of the air cooling device.
Figure 3:
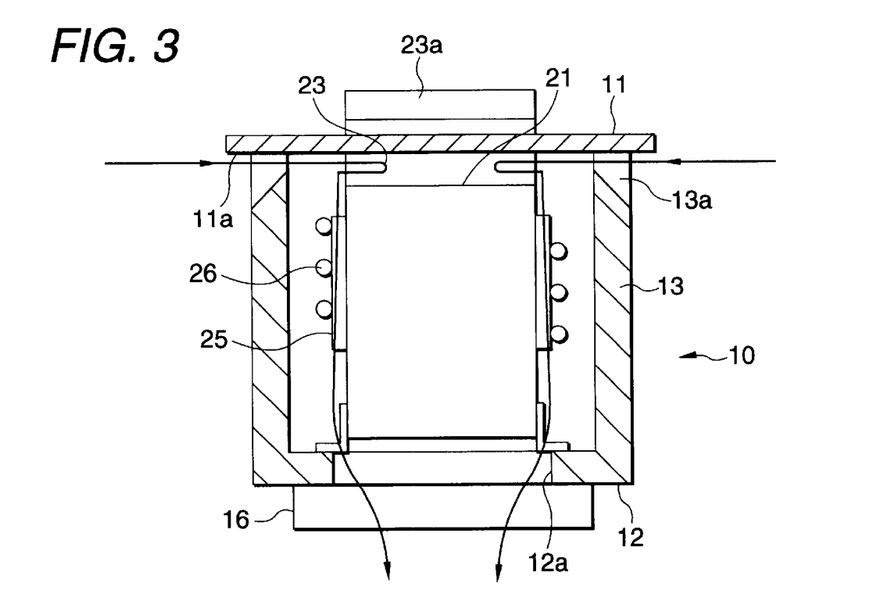
FIG. 3 is a section view of the box.

An air-cooling device for a coil for urinary incontinence treatment of an embodiment of the invention will be described with reference to FIGS. 1 to 4. As shown in FIG. 3, the air-cooling device is configured as a rectangular parallelopiped box 10 which is made of synthetic resin, and which houses a coil 26 having a core 20 to internally perform forced air-cooling. In the core 20, as shown in FIG. 2, two J-type cores which are configured by grain-oriented silicon steel, and which has a section of 5×5 cm are combined into an E-type core, and front and rear side legs 23 are taller than the center leg 21 so as to protrude from a box upper board 11. A conductive member 26a is wound around the center leg 21 so that turns are separated from each other, and via rod-like spacers 25 so as to form a gap 25a between the member and the center leg 21, thereby configuring the coil 26. End faces 23a of the side legs 23 are inclinedly formed so as to be opposed to each other. In consideration of the heat radiation property, and electrically insulative black coating composition is applied to the core 20 and the coil 26. The box 10 has a shape which forms a small gap with respect to the outer periphery of the core 20 of a size that allows the core to be set in a seat region for the patient, and on which the patient can sit. As shown in FIGS. 2 and 3, air flows through the air way 13a by suction of the blower 16 and cools the end face 21a of the center leg 21. After that the air flows through the space between the coil 26 and the core 21 made by the spacer 25, cooling the coil 26 and the core 21. Further, the air is exhausted by the blower 16 through the air way 12a in the bottom board 12 to outside of the box 10.

As shown in FIG. 3 an air way 12a of a size corresponding to the section.shape of the coil 26 is formed in a center region of a bottom board 12 of the box, i.e., below the coil 26. A blower 16 which sucks air in the box 10 is attached to the outside with respect to the air way. A gap of about 5~10 mm is formed between an end face 21a of the center leg 21 and the box upper board 11. An air way 13a which is opposed to the coil 26 and which has a size corresponding to the width of the coil is formed in each of box side boards 13 on both lateral sides with respect to the gap. The lower face of each air way 13a is formed as an inclined surface so as to gradiently increase the width of air flow path toward the outside as shown in FIG. 3. Namely, the air way has a substantially same width of the gap defined between the end face 21a and the box upper board 11 in an inner side of the box side board 13, and has approximately 10~20 mm in an outside of the box side board 13.

As shown in FIG. 1(b), the box 10 is, for example, a rectangular parallelopiped in which the depth is 50 cm and the width and the height are 20 cm. The air way 13a has a width of 20 cm and a length of 1 cm. The flexible conductive member constituting the coil 26 is configured by an insulated electric wire, a rectangular copper wire, a copper pipe, or a litz wire in which the skin effect can be reduced so as to reduce the power consumption. The conductive member has a sectional area of 40 to 500 mm$^2$. When a conductive member having a large sectional area is required, such a conductive member is produced by binding plural conductive members. Alternatively, the position of air way 13a is equal to or higher in height than that of the coil 26. The air volume of the discharging blower 16 is about 10 m$^3$/min. when the coil 26 is energized at the peak current of 5,000 A and the maximum power consumption of 1.5 kVA.

Figure 4:
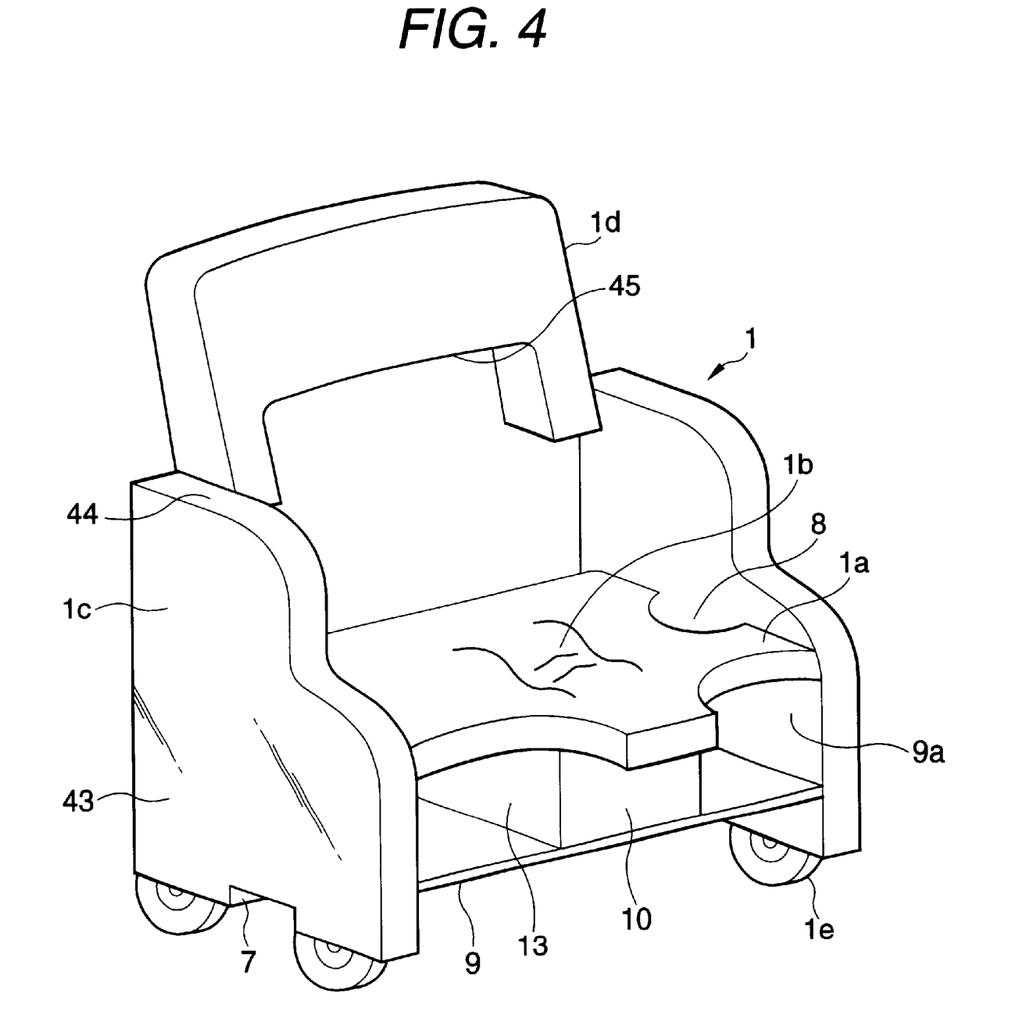
FIG. 4 is a perspective view of a chair into which the box is incorporated as an urinary incontinence treatment apparatus.

A chair 1 into which the box 10 is mounted to constitute an urinary incontinence treatment apparatus is configured in the following manner. As shown in FIG. 4, a seat 1a is attached between side portions 1c on both sides. Each side portion has a leg 43 on which casters 1e are downward disposed, and an armrest 44. A backrest 1d is attached to rear portions of the side portions 1c so as to form an opening 45. Alternatively, an urinary incontinence treatment apparatus may be configured by mounting the box 10 into a bed.

Figure 1:
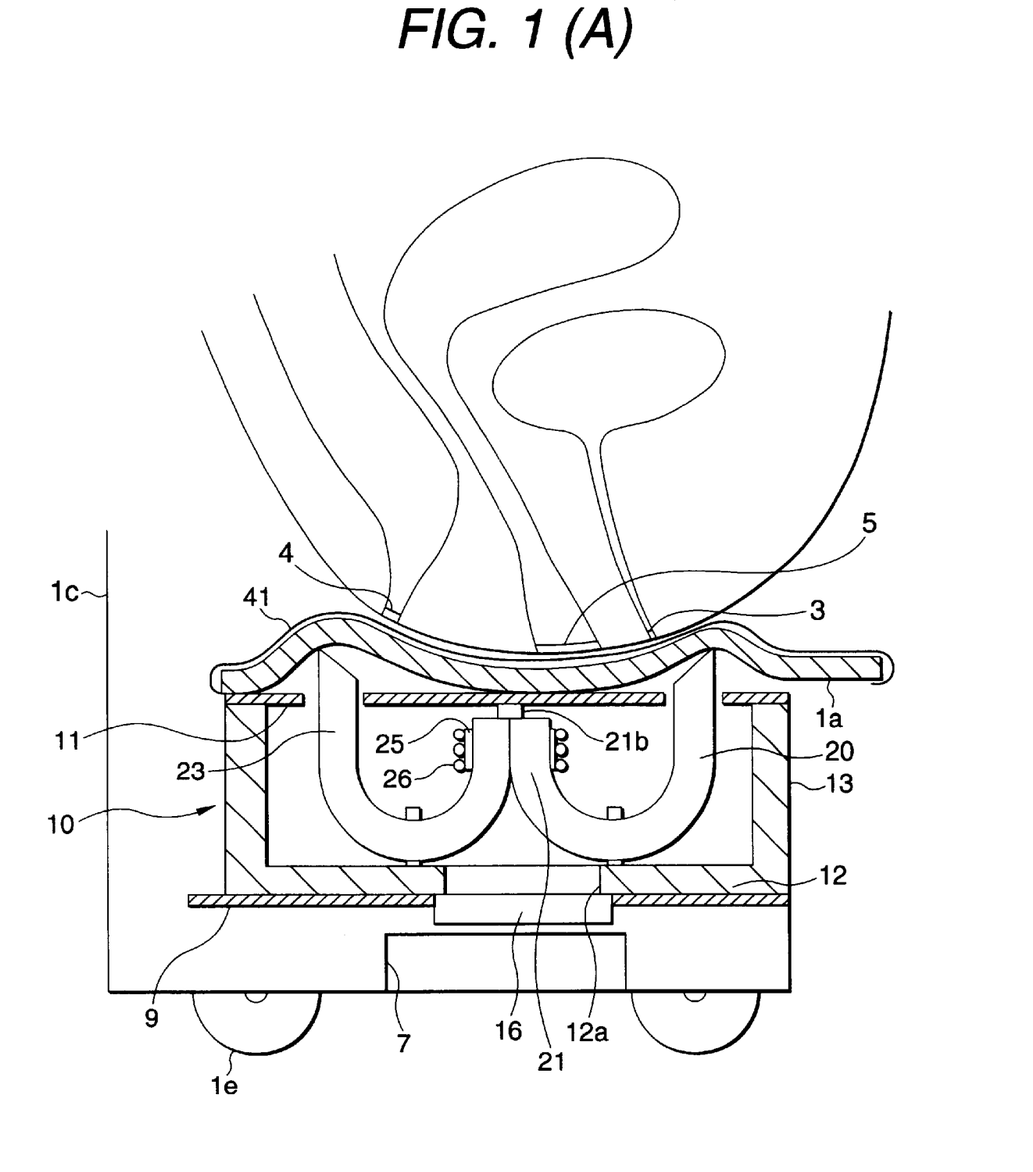
FIG. 1(a) is a section view of an air-cooling device for a coil for urinary incontinence treatment which is an embodiment of the invention, taken in an anteroposterior direction.
FIG. 1(b) is a perspective view of a box of the present invention

In the plate-like seat 1a, as shown in FIGS. 1 and 4, formed is a saddle portion 1b which has a concave surface that is recessed in an anteroposterior direction so as to correspond to a curved face of a region of a woman extending from a front of the urethral orifice 3 to a rear of the anus 4 with interposing clitoris 5 therebetween, which is covered with a cushion sheet 41, and which is curvedly raised in a lateral direction in a center area. The seat a forward protrudes in a center region in a lateral direction from the side portions 1c. Air ways 8 are formed on both sides of the seat 1a and above the air ways 13a, respectively. A partition board 9 is bridged between lower portions of the side portions 1c to support the box 10 so that the blower 16 is fitted into a center opening of the partition board and the air way 13a are exposed. The box upper board 11 is attached to the rear face of the seat 1a. The blower 16 slightly downward protrudes from the partition board 9. A cutout portion 7 is formed in a further lower area of each of the side portions 1c. The partition board 9 has a function for preventing the warm air, which is exhausted by the blower 16, from being entered into the box 10. Further, the box upper board 11 has an extended portion at the end thereof for guiding the air flow through the air way 13a into the box 10. In order to retain the air pathway by stably remaining the gap between the box upper board 11 and the end face 21a of the center leg 21, a particular spacer made of heat-proof plastic may be placed.

When the patient sits on the saddle portion 1b of the seat 1a as shown in FIG. 1(a) and the above-mentioned pulse current or alternating current is supplied to the coil 26, magnetic fluxes are concentratedly generated between the end face 21a of the center leg 21 and the opposed end faces 23a of the side legs 23 and in the living body in the region from the front area of the urethral orifice 3 to the rear area of the anus 4, without causing the core 20 to saturate. The living body is efficiently stimulated by induced large eddy currents. Since the center leg 21 is lower in level than the side legs 23, the magnetic fluxes stimulate an effective portion without unnecessarily reaching an upper portion. Since the side portions 1c are recessed from the front end of the seat 1a, the treatable portion can be widened to a required region by stretching the femoral regions, thereby enhancing the treatment effect. Because of the box upper board 11 which is electrically insulative and nonmagnetic, the magnetic fluxes are not confined into the box 10, and the patient is prevented from suffering an electric shock. Heat due to the electric resistance of the coil 26 and the eddy currents in the center leg 21 is dissipated by the forced air-cooling based on suction by the blower 16.

Specifically, as shown in FIG. 4, air which is sucked from the air ways 13a and the vicinities thereof or the air ways 8 into the box 10 pass over the vicinity of the center leg 21 and is then discharged via the air way 12a to the side below the partition board 9. The hot air is dissipated through the vicinity of the partition board 9 or the cutout portions 7. The inflow air passes over the whole periphery of the coil 26 which is separated from the core by the spacers 25, and at the same time the center leg 21 also is cooled. Also the gap between the end face 21a and the seat 1a which is above the end face is sufficiently air-cooled. Although the air sucked by the blower 16 is gradually heated as advancing toward the lower side, an upper portion of the coil 26 which is closer to the living body is efficiently cooled by air which is relatively cooler. In both sides of the box 10, ducts 9a which elongate in an anteroposterior direction are formed by the box side boards 13, the side portions 1c, the seat 1a and the partition board 9. Air pathways through which air flows into the air ways 13a from the front and rear end of the duct are formed so as to exert a cooling function on the box side boards 13. The air discharged from the blower 16 is blocked by the partition board 9 and the side portions 1c, so that hot air is largely suppressed from being circulated into the air ways 13a.

It was checked that, when the outside air temperature is 28° C. or lower during a treatment time period of 15 minutes, the coil 26 can be maintained to 40° C. or lower and the seat 1a can be maintained to 30° C. or lower. Therefore, the patient can be surely prevented also from suffering low-temperature burn. Even when the chair 1 is placed in a corner of a room, the presence of the cutout portions 7 can sufficiently prevent temperature rise due to stagnation of hot air from occurring.

When a blower is additionally disposed in a front or rear end portion of each of the ducts 9a which are respectively formed on the sides of the box side boards 13, the cooling function can be further enhanced. When the box bottom board 12 is extended in area so as to function as a partition board, the partition board 9 may be omitted.

Figure 5:
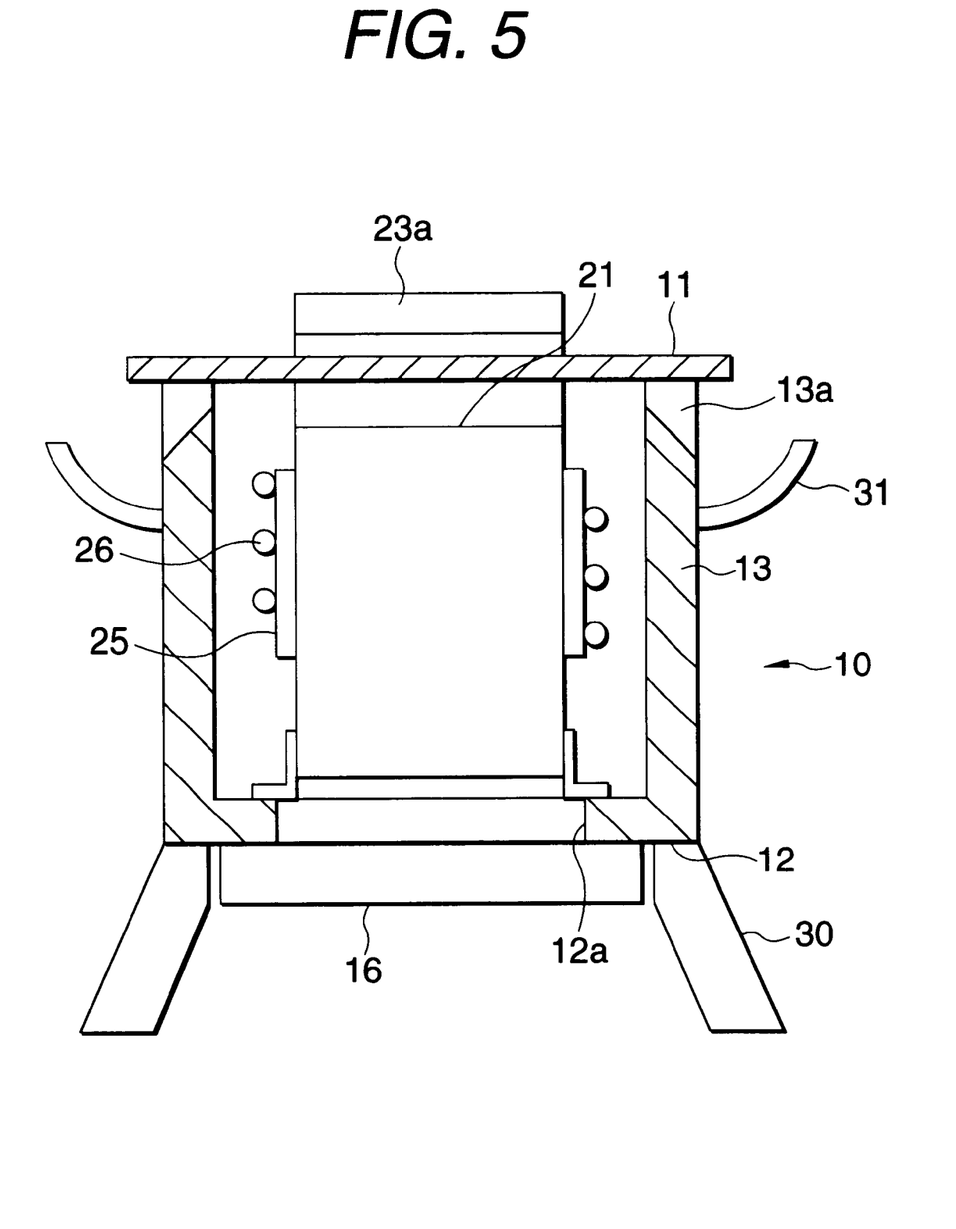
FIG. 5 is a section view of a chair serving as an urinary incontinence treatment apparatus of another embodiment using the box.

FIG. 5 shows an embodiment in which the box 10 itself having a shape enabling the patient to sit thereon functions as a chair-type urinary incontinence treatment apparatus. Legs 30 for placing the box 10 on a floor under a state where the blower 16 is separated from the floor are downward disposed in the four corners of the box bottom board 12, respectively. Visors 31 are respectively formed on the lower edges of the air ways 13a of the box side boards 13 in order to prevent the air ways from being closed as a result of sitting of the patient, and also to block hot air pathways between the air ways 13a and the blower 16. Such visors may be formed on the bottom board 12 so as to similarly block hot air pathways. In this apparatus, the end faces 23a of the side legs 23 are in direct contact with or close to the living body portion in the crotch region. From the viewpoint of temperature rise, therefore, the power supplied to the coil 26 may be reduced as required under assumption that the treatment time period is prolonged.

Figure 6:
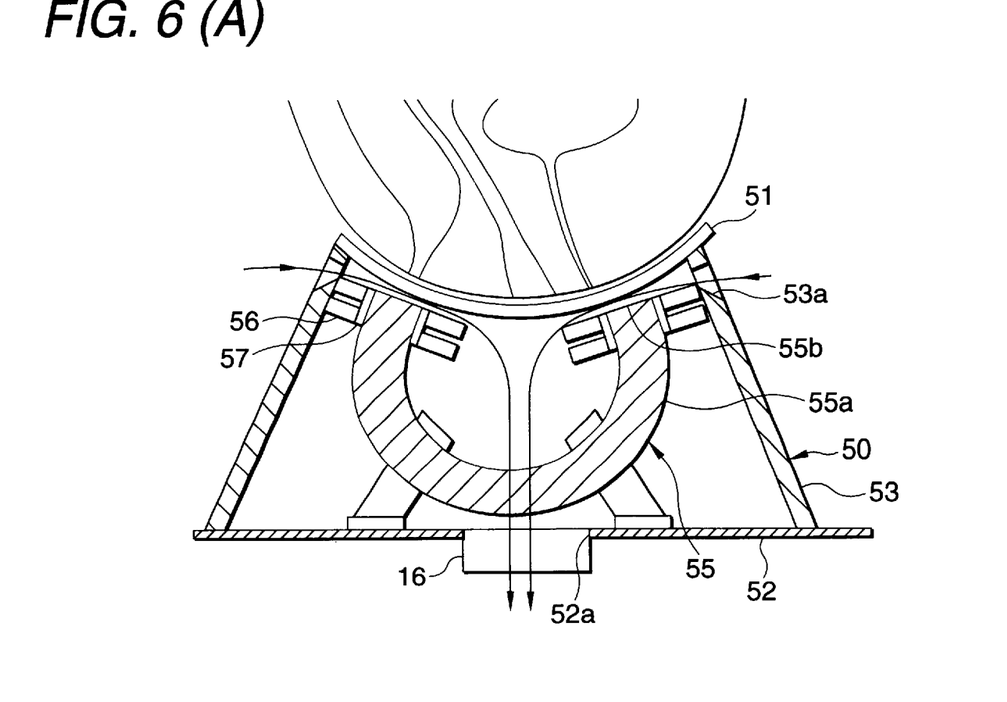
FIG. 6 shows an air-cooling device of another embodiment for a cored coil.

FIG. 6A shows another embodiment in the case of a cored coil. In the embodiment, a C-type core 55 is housed in a box 50 having a box upper board 51 which is formed into a concave surface corresponding to the curvature of the portion to be treated. A coil 56 is wound around an upper portion of each of front and rear side legs 55a with forming a gap between turns, and via spacers 57 that are intermittently placed. An air way 52a is formed in a box bottom board 52. The blower 16 is attached to the outside with respect to the air way. An air way 53a is formed in a region of each of front and rear side boards 53 and opposed to the coil 56. End faces 55b of the front and rear side legs 55a extend along the box upper board 51 with forming a gap of about 5~10 mm therebetween, so as to be inclined and opposed to each other.

The outside air flows into the box through the air ways 53a as a result of suction of the blower 16, and the whole periphery of the coil 56 is exposed to the flow of the outside air. The outside air flows into also through gaps between the box upper board 51 and the front and rear side boards 53. The outside air is then discharged through the air way 52a. Legs may be downward disposed on the box 50 or a backrest for positioning may be upward disposed, so that the box 50 is configured as a chair-type urinary incontinence treatment apparatus. Alternatively, the box may be configured so as to be mounted into a seat portion of a chair which is separately produced. In place of the c-type core 55, a U-type core in which front and rear side legs are similarly directed to the box upper board may be used.

In the case of the E-type core 20 shown in FIG. 1(a) magnetic fluxes are concentrated into the vicinity of the clitoris 5 of a woman. By contrast, in the case of the C-type core 55, magnetic fluxes are concentrated into the vicinity of the anus 4 or the urethral orifice 3. Therefore, a coil may be wound also around the front and rear side legs 23 of the E-type core, and the coils and the coil 26 of the center leg 21 may be selectively energized by a switch in order to select a portion to be stimulated or cope with differences in physical constitution. Although the production cost is increased, plural cored coils or air-core coils which are different from one another in magnetic flux generating position may be prepared, and the coils may be selectively energized in accordance with a portion to be stimulated or the physical constitution.

As shown in FIG. 6B, in place of the spacers 57, heat radiating fins 57a which have grooves for holding the coils 56 and through which heat is radiated from the coil and the core 55 may be attached to the core 55 in radial directions. Assuming that the coils 56 and the core 55 are electrically insulative, the radiating fins 57a may be made of a metal having an excellent heat radiation property such as aluminum or copper, a diamagnetic metal, carbon, or the like. In order to prevent eddy currents from flowing, preferably, the fins are formed as thin as possible. From the viewpoint of the heat radiating efficiency, preferably, the fins may have a shape of a larger area which is downward extended to a lower end position of the blower flow so as to produce a sufficient temperature gradient. Alternatively, the core 55 may be concaved and convexed so as to increase the heat radiating area. As described above, the coil 26 may be configured by an insulated electric wire, a rectangular copper wire, a copper pipe, a litz wire, or the like.

Figure 7:
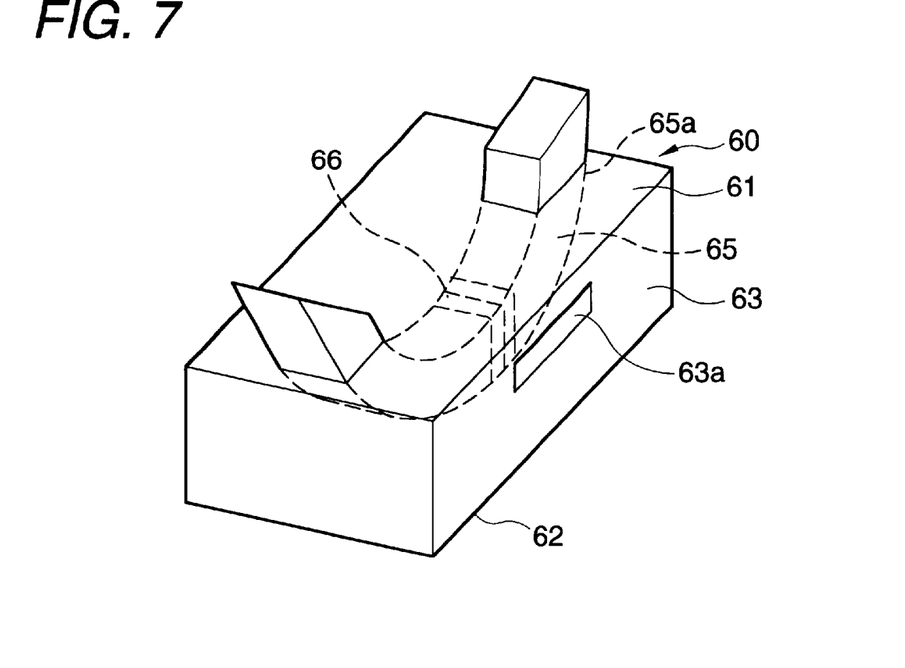
FIG. 7 is a perspective view of an air-cooling device of a further embodiment for a cored coil.

FIG. 7 shows a further embodiment in the case of a cored coil. A C-type core 65 is housed in a rectangular parallelopiped box 60. A coil 66 is wound around a bottom portion of the core with forming a gap between turns, and between the coil and the core 65. An air way (not shown) is formed in a bottom board 62 of the box and below the coil 66, and a blower (not shown) is attached to the outside with respect to the air way upper portions of front and rear side legs 65a protrude from an upper board 61 of the box, and their end faces are inclined so as to be opposed to each other. An air way 63a is formed in each of lateral side boards 63 of the box and above the coil 66. The outside air which flows into the box through the air ways cools the coil 66 and the core 65 with starting from their upper portions which are closer to the living body, and is then discharged by means of suction from the air way which is positioned immediately below the core. The embodiment is simple in structure, and hence may be preferably used in a small apparatus which is not required to perform stimulation at a high output level. Alternatively, the blower may be configured as a discharge type so as to blow air to the coil 66 in the neighborhood. The depth of the box 60 may be reduced so that the front and rear side legs 65a protrude from front and rear box side boards 63 to a level which is higher than the box upper board 61.

Figure 8:
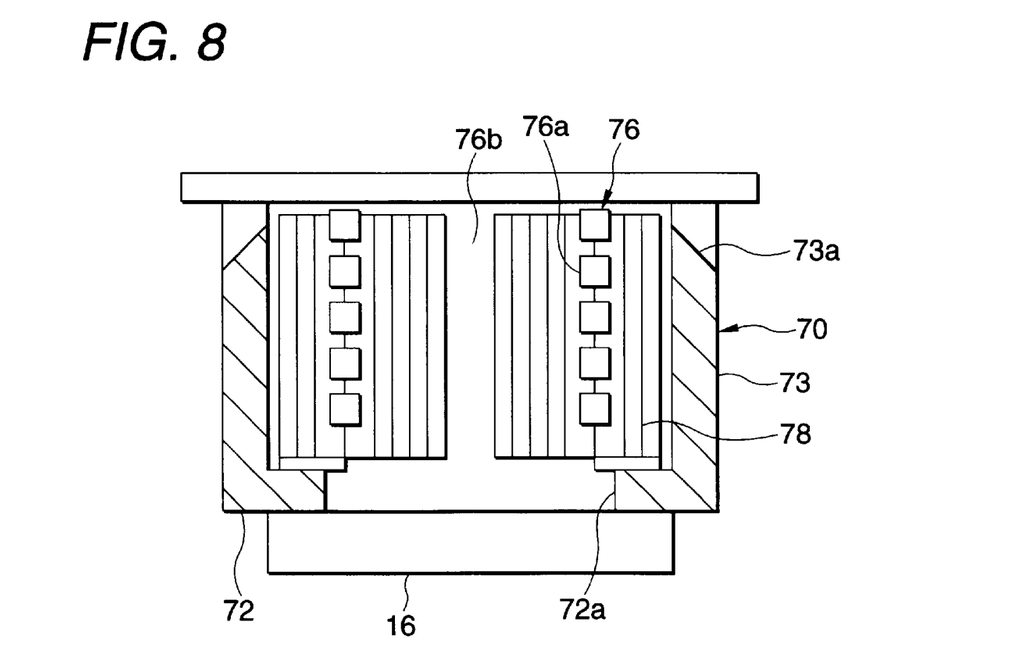
FIG. 8 is a section view of an air-cooling device of an embodiment for an air-core coil according to the invention.

FIG. 8 shows an embodiment in the case of an air-core coil. A coil 76 is housed in a longitudinally elongated rectangular parallelopiped box 70. In the coil, an insulation covered black conductive member 76a is solenoidally wound in the direction toward a bottom board 72 of the box with forming a gap between turns. The coil is pressingly held in radial directions by plural heat radiating fins 78 which are made of aluminum and insulation coated into black. Air ways 73a which are opposed to the coil 76, and which have a width corresponding to the diameter of the coil are formed in upper portions of lateral side boards 73 of the box. The air which flows into the box through the air ways is passed through the air core 76b and between the heat radiating fins 78 to air-cool the coil 76 in which gaps are formed between turns, and then discharged through the air way 72a. The heat radiating fins 78 are arranged along the direction of magnetic fluxes. Therefore, heat generation due to eddy currents is very small in degree. Since the embodiment is configured as an air-cored coil, the efficiency is lower than that in the case of a cored coil. However, it is possible to cope with this by suppressing the input power and correspondingly prolonging the treatment time period. In the case where the pulse width is constant, when the stimulation frequency is set to about 20 to 50 Hz which is effective against stress incontinence, the efficiency is lower than that in the case of a cored coil, so that the power consumption is larger, but the embodiment can be used particularly for treatment of urge incontinence in which the frequency is about 5 to 10 Hz, at appropriate power consumption and temperature rise. The embodiment can be reduced in weight by elimination of a core, and preferably configured also as a household treatment apparatus. The heat radiating fins 78 may be further downward elongated toward the air way 72a so as to increase temperature gradient, or made of a thin magnetic material so as not to disturb magnetic fluxes.

Figure 9:
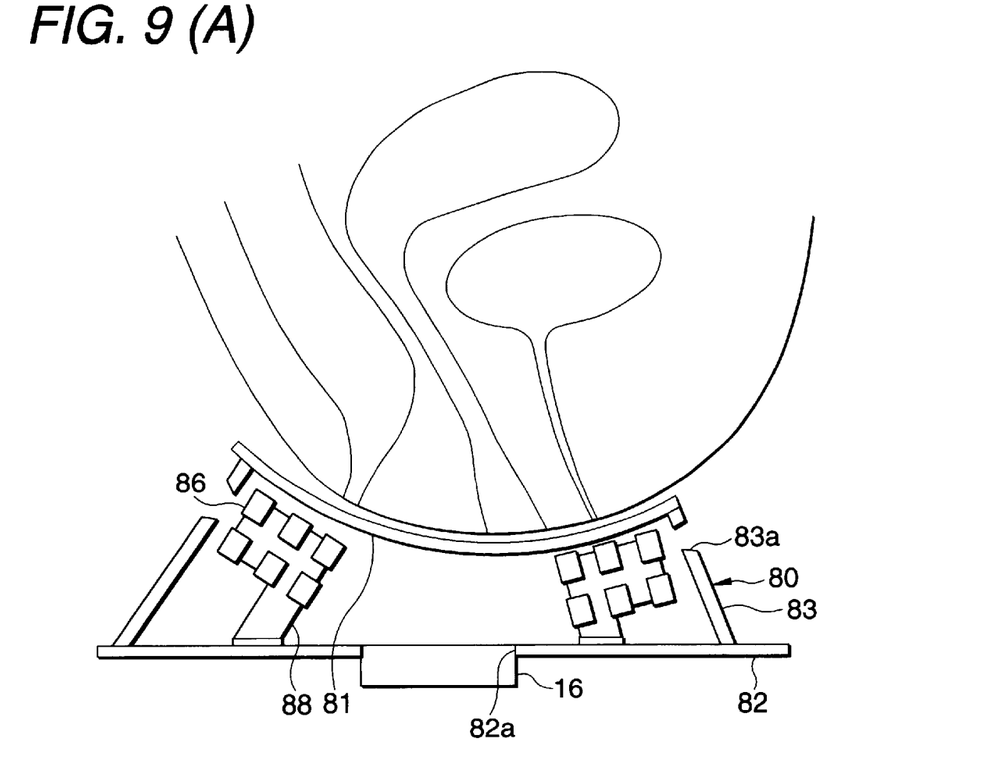
FIG. 9 shows an air-cooling device of another embodiment for an air-core coil.

FIG. 9 shows another embodiment in the case of an air-core coil. A coil 86 consisting of three layers of two turns is housed in a box 80 having a box upper board 81 which is formed into a concave surface. The coil is wound in the direction toward a bottom board 82 of the box so as to have an air core in the center. The coil is set in grooves of plural radial heat radiating fins 88 which function also as a supporting member, so as to form a gap over a whole periphery of a conductive member.

The outside air which flows into the box through air ways 83a formed in upper portions of front and rear box side boards 83 moves along the heat radiating fins 88 to cool the whole periphery of the conductive member constituting the coil 86, and then forcedly discharged through an air way 82a of a box bottom board 82 which is positioned below the air core. The upper face of the front side of the coil 86, and that of the rear side are inclined along the box upper board 81 to be opposed to each other, so as to be closer to the living body. As a result, the efficiency can be made higher than the case of the box 70 of FIG. 8.

Figure 10:
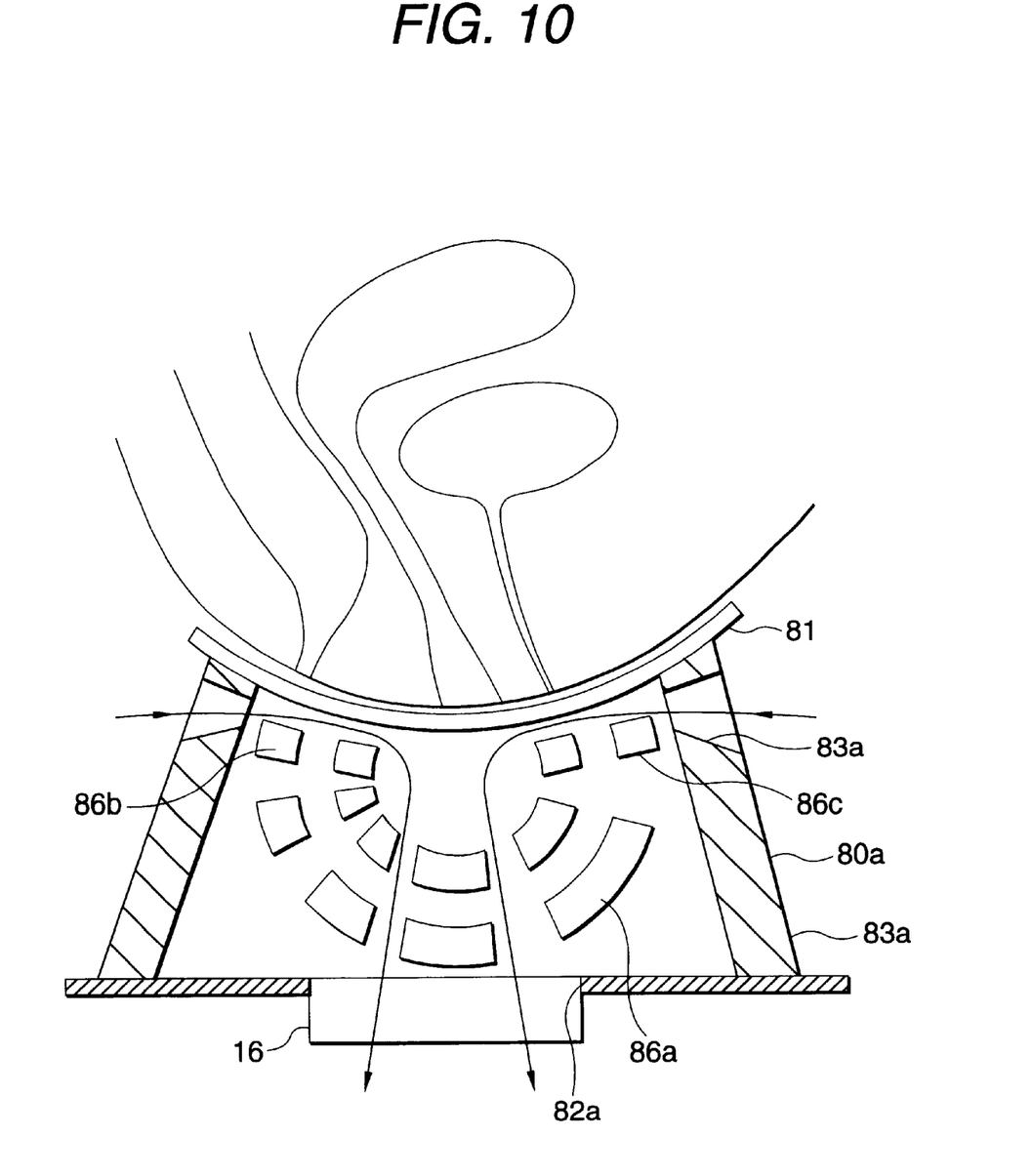
FIG. 10 is a section view of a box of a further embodiment for an air-core coil.

FIG. 10 shows a further embodiment in the case of an air-core coil. A coil 86a consisting of one layer of a U-like winding direction is housed in a box 80a in which box side boards 83b are made taller as compared with those of the box 80 of FIG. 9. An upper face 86b on the side of the winding start end, and an upper face 86c on the side of the winding finish end extend along the box upper board 81 so as to be opposed to each other, thereby concentrating magnetic fluxes into the vicinities of the anus and the urethral orifice. As compared with the apparatus of FIG. 6, the degree of stimulation is reduced. Therefore, the embodiment is suitable in a small apparatus in which the treatment time period is set to be long, particularly for treating urge incontinence.

Figure 11:
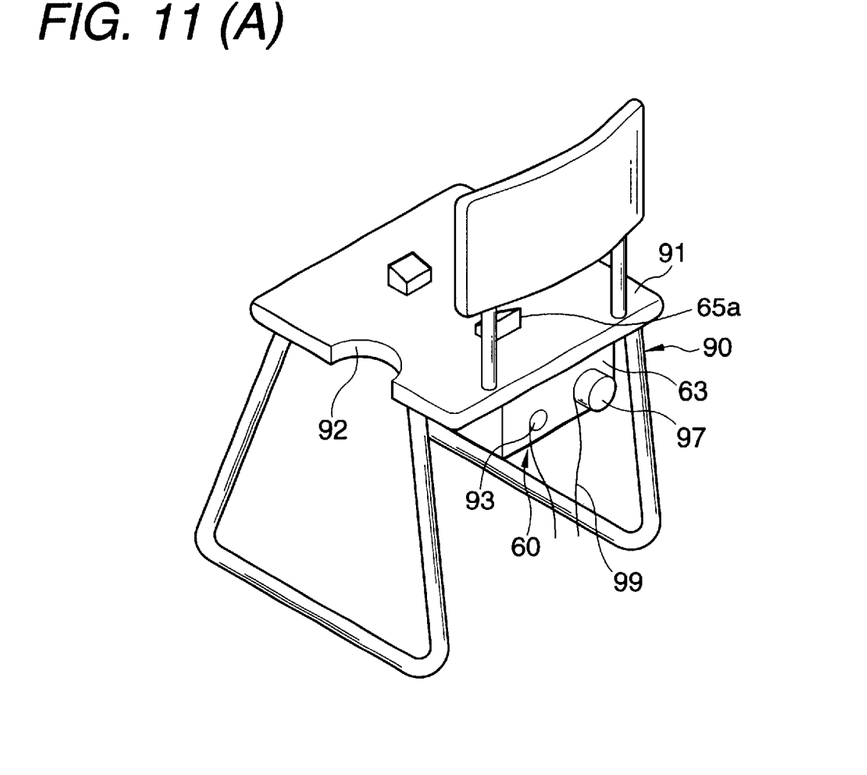
FIG. 11 shows an air-cooling device of an embodiment for a coil in which a pipe-shaped conductor member is wound, according to the invention.

FIG. 11 shows an embodiment of an urinary incontinence treatment apparatus in which a coil configured by winding a pipe-shaped conductor member is cooled. For example, the box 60 which has been described with reference to FIG. 7 is attached to a seat portion 91 of a chair 90 having legs configured by a pipe. The front and rear side legs 65a slightly protrude from the seat portion 91. The coil 66 is configured by the conductor member which is a copper pipe. The ends of the coil are guided by the box side boards 63 and then connected to power supply wires 99, respectively. One end 93 of the coil 66 is opened in the atmosphere, and a blower 97 is attached to the other end. Visors 94 are formed on the lower edges of the air ways 63a, and cutout portions 92 are formed in regions of the seat portion 91 which are above the air ways 63a, respectively. According to this configuration, the outside air flows into the air ways 63a from the lateral and upper sides by suction of the blower 16, and the coil 66 is air-cooled in the box 60. Furthermore, the coil is force-cooled also by blowing the outside air by the blower 97 into the pipe-like conductor member to cause the air to circulate through the interior of the coil.

According to the first to tenth aspect of the invention, the air-core coil or the cored coil is exposed in the box to the flow of the outside air produced by the blower, whereby forced cooling is efficiently performed on the coil and the core.

According to the eleventh or twelfth aspect of the invention, the air-cooling device for a coil and using the box can be easily configured as an urinary incontinence treatment apparatus by itself or incorporating the device into a chair.

According to the thirteenth aspect of the invention, the coil is configured by a pipe-shaped conductor member and the interior of the coil is force-cooled by the outside air, whereby a stronger forced air-cooling device can be realized.

What is claimed is:

1. An air-cooling device in a urinary incontinence treatment device comprising:
    a coil to which pulse current or alternating current is supplied, to generate magnetic fluxes toward an area from a front of an urethral orifice to a rear of an anus for inducing eddy currents in a living body,
    the coil accommodated in a box having an upper board which is electrically insulative and nonmagnetic, said coil being wound along said upper board;
    a first air way formed in a bottom board of said box;
    a blower attached to said first air way, and
    a second air way formed in side boards of said box opposed from each other.

2. An air-cooling device for a coil for urinary incontinence treatment according to claim 1, wherein a position of said second air way is equal to or higher in height than that of said coil.

3. An air-cooling device for a coil for urinary incontinence treatment according to claim 1, wherein said upper board is formed to have a concave surface, and an upper face of said coil is inclined along said upper board.

4. An air-cooling device for a coil for urinary incontinence treatment according to claim 1, wherein a conductive member is wound around said coil so as to form a gap over a whole periphery of said coil.

5. An air-cooling device for a coil for urinary incontinence treatment according to claim 1, further comprising:
    heat radiating fins attached to said coil extending in radial directions.

6. An air-cooling device for a coil for urinary incontinence treatment according to claim 1, wherein legs are downward disposed on said bottom board of said box, for placing said box under a state where said blower is separated from a floor to enable said box to function as a chair.

7. An air-cooling device for a coil for urinary incontinence treatment according to claim 1, further comprising:
    a seat portion mounted on said box;
    ducts respectively formed between said side boards and said side portions opposed to said side boards, said blower placed adjacent to said bottom board of said ducts;
    cutout portions, communicating with said ducts, formed in side end portions of said seat portion, respectively, and
    ventilation cutout portions formed in intermediate regions in anteroposterior directions of said side portions and in side areas of said blower.

8. An air-cooling device for a coil for urinary incontinence treatment according to claim 1, wherein said coil is defined by a pipe-shaped conductor member, ends of said conductor member are connected to a side face of said box, one of said ends is opened in air, and a blower is attached to another one of said ends.

9. An air-cooling device in a urinary incontinence treatment device, comprising:
    a coil to which pulse current or alternating current is supplied to generate magnetic fluxes toward an area from a front of an urethral orifice to a rear of an anus for enducing eddy currents in a living body;
    a box having an upper board which is electrically insulative and nonmagnetic;
    a core having front and rear side legs, and a coil wound around said core, said core being accommodated in said box, said front and rear legs elongating toward said box upper board,
    a first air way formed in a bottom board of said box;
    a blower attached to said first air way and
    a second air way formed in a side board of said box, an air flow path defined between said first air way and said second air way through said core and said coil.

10. An air-cooling device for a coil for urinary incontinence treatment according to claim 4, wherein said core has an E-like shape in which a center leg is formed between said front and rear side legs, said coil being wound around said center leg, and
    wherein said second air way is formed in side boards of said box opposed from each other.

11. An air-cooling device for a coil for urinary incontinence treatment according to claim 9, wherein a conductive member is wound around said coil so as to form a gap over a whole periphery of said coil.

12. An air-cooling device for a coil for urinary incontinence treatment according to claim 9, wherein said front and rear side legs protrude from said box to a level which is higher than said upper board.

13. An air-cooling device for a coil for urinary incontinence treatment according to claim 9, further comprising:
    heat radiating fins attached to said core extending in radial directions.

14. An air-cooling device for a coil for urinary incontinence treatment according to claim 9, wherein a position of said second air way is equal to or higher in height than that of said coil.

15. An air-cooling device for a coil for urinary incontinence treatment according to claim 9, further comprising:
    heat radiating fins attached to said coil extending in radial directions.

16. An air-cooling device for a coil for urinary incontinence treatment according to claim 9, wherein legs are downward disposed on said bottom board of said box, for placing said box under a state where said blower is separated from a floor to enable said box to function as a chair.

17. An air-cooling device for a coil for urinary incontinence treatment according to claim 4, further comprising:
   a seat portion mounted on said box;
   ducts respectively formed between said side boards and said side portions opposed to said side boards, said blower placed to said bottom board of said ducts;
   cutout portions, communicating with said ducts, formed in side end portions of said seat portion, respectively, and
   ventilation cutout portions formed in intermediate regions in anteroposterior directions of said side portions and in side areas of said blower.

18. An air-cooling device for a coil for urinary incontinence treatment according to claim 4, wherein said coil is defined by a pipe-shaped conductor member, ends of said conductor member are connected to a side face of said box, one of said ends is opened in air, and a blower is attached to another one of said ends.

19. An apparatus for supplying magnetic fluxes to a living body, comprising:
   at least one coil, which supplies magnetic fluxes to a living body;
   a box, which accommodates that at least one coil therein, the box including a first board and a second board;
   a first air way, formed in the first board;
   a blower, attached to the first air way; and
   a second air way, formed in the second board such that air flows to the at least one coil directly.

20. The apparatus according to claim 19, wherein a litz wire forms the coil.

21. An apparatus for supplying magnetic fluxes to a living body, comprising:
   at least one coil, which supplies magnetic fluxes to a living body;
   a box, which accommodates the at least one coil therein, the box including a first board and a second board;
   at least one core, wound by the at least one coil and accommodated in the box;
   a first air way, formed in the first board;
   a blower, attached to the first air way; and
   a second air way, formed in the second board such that air flows to the at least one coil directly.

22. The apparatus according to claim 21, wherein a litz wire forms the coil.

23. An apparatus for performing incontinence treatment by supplying magnetic fluxes to a living body, comprising:
   a seat portion, on which a living body is seated;
   at least one coil, which supplies magnetic fluxes to the living body;
   a box, provided under the seat portion to accommodate the at least one coil therein; and
   an air-cooling device, which introduces air from outside the box and blows the air to the at least one coil directly.

24. The apparatus according to claim 23, wherein a litz wire forms the coil.

25. An apparatus for performing incontinence treatment by supplying magnetic fluxes to a living body, comprising:
   a seat portion, on which a living body is seated;
   at least one coil, which supplies magnetic fluxes to the living body;
   a box, provided under the seat portion to accommodate the at least one coil therein, the box including a first board and a second board;
   a first air way, formed in the first board;
   a blower, attached to the first air way; and
   a second air way, formed in the second board such that air flows to the at least one coil directly.

26. The apparatus according to claim 25, wherein a litz wire forms the coil.

27. An apparatus for performing incontinence treatment by supplying magnetic fluxes to a living body, comprising:
   a seat portion, on which a living body is seated;
   at least one coil, which supplies magnetic fluxes to the living body;
   a box, provided under the seat portion to accommodate the at least one coil therein;
   at least one core, wound by the at least one coil and accommodated in the box; and
   an air-cooling device, which introduces air from outside the box and blows the air to the at least one coil and the at least one core directly.

28. The apparatus according to claim 27, wherein a Itiz wire forms the coil.

29. An apparatus for performing incontinence treatment by supplying magnetic fluxes to a living body, comprising:
   a seat portion, on which a living body is seated;
   at least one coil, which supplies magnetic fluxes to the living body;
   a box, provided under the seat portion to accommodate the at least one coil therein, the box including a first board and a second board;
   at least one core, wound by the at least one coil and accommodated in the box;
   a first air way, formed in the first board;
   a blower, attached to the first air way; and
   a second air way, formed in the second board such that air flows to the at least one coil directly.

30. The apparatus according to claim 29, wherein a litz wire forms the coil.

31. An air-cooling device for a coil in a urinary incontinence treatment device to which pulse current or alternating current is supplied, to generate magnetic fluxes toward an area from a front of an urethral orifice to a rear of an anus for inducing eddy currents in a living body, comprising:
   a coil accommodated in a box having an upper board which is electrically insulative and nonmagnetic, said coil being wound along said upper board;
   a first air way formed in a bottom board of said box;
   a blower attached to said first air way; and
   a second air way formed in side boards of said box opposed from each other;
   wherein said upper board is formed to have a concave surface, and an upper face of said coil is inclined along said upper board.

32. An air-cooling device for a coil in a urinary incontinence treatment device, to which pulse current or alternating current is supplied, to generate magnetic fluxes toward an area from a front of an urethral orifice to a rear of an anus for inducing eddy currents in a living body, comprising:
   a box having an upper board which is electrically insulative and nonmagnetic;

a core having front and rear side legs, and a coil wound around said core, said core being accommodated in said box, said front and rear legs elongating toward said box upper board;

a first air way formed in a bottom board of said box;

a blower attached to said first air way; and a second air way formed in a side board of said box, an air flow path defined between said first air way and said second air way through said core and said coil, wherein said core has an E-like shape in which a center leg is formed between said front and rear side legs, said coil being wound around said center leg, and wherein said second air way is formed in side boards of said box opposed from each other.

33. An air-cooling device for a coil in a urinary incontinence treatment device, to which pulse current or alternating current is supplied, to generate magnetic fluxes toward an area from a front of an urethral orifice to a rear of an anus for inducing eddy currents in a living body, comprising:

a box having an upper board which is electrically insulative and nonmagnetic;

a core having front and rear side legs, and a coil wound around said core, said core being accommodated in said box, said front and rear legs elongating toward said box upper board;

a first air way formed in a bottom board of said box;

a blower attached to said first air way; and a second air way formed in a side board of said box, an air flow path defined between said first air way and said second air way through said core and said coil, wherein said front and rear side legs protrude from said box to a level which is higher than said upper board.

34. An air-cooling device for a coil in a urinary incontinence treatment device to which pulse current or alternating current is supplied, to generate magnetic fluxes toward an area from a front of an urethral orifice to a rear of an anus for inducing eddy currents in a living body, comprising:

a coil accommodated in a box having an upper board which is electrically insulative and nonmagnetic, said coil being wound along said upper board;

a first air way formed in a bottom board of said box;

a blower attached to said first air way; and a second air way formed in side boards of said box opposed from each other;

wherein legs are downward disposed on said bottom board of said box, for placing said box under a state where said blower is separated from a floor to enable said box to function as a chair.

35. An air-cooling device for a coil in a urinary incontinence treatment device to which pulse current or alternating current is supplied, to generate magnetic fluxes toward an area from a front of an urethral orifice to a rear of an anus for inducing eddy currents in a living body, comprising:

a coil accommodated in a box having an upper board which is electrically insulative and nonmagnetic, said coil being wound along said upper board;

a first air way formed in a bottom board of said box;

a blower attached to said first air way;

a second air way formed in side boards of said box opposed from each other;

a seat portion mounted on said box;

ducts respectively formed between said side boards and said side portions opposed to said side boards, said blower placed adjacent to said bottom board of said ducts;

cutout portions, communicating with said ducts, formed in side end portions of said seat portion, respectively; and ventilation cutout portions formed in intermediate regions in anteroposterior directions of said side portions and in side areas of said blower.

36. An air-cooling device for a coil in a urinary incontinence treatment device to which pulse current or alternating current is supplied, to generate magnetic fluxes toward an area from a front of an urethral orifice to a rear of an anus for inducing eddy currents in a living body, comprising:

a coil accommodated in a box having an upper board which is electrically insulative and nonmagnetic, said coil being wound along said upper board;

a first air way formed in a bottom board of said box;

a blower attached to said first air way; and a second air way formed in side boards of said box opposed from each other;

wherein said coil is defined by a pipe-shaped conductor member, ends of said conductor member are connected to a side face of said box, one of said ends is opened in air, and a blower is attached to another one of said ends.

37. An air-cooling device for a coil in a urinary incontinence treatment device, to which pulse current or alternating current is supplied, to generate magnetic fluxes toward an area from a front of an urethral orifice to a rear of an anus for inducing eddy currents in a living body, comprising:

a box having an upper board which is electrically insulative and nonmagnetic;

a core having front and rear side legs, and a coil wound around said core, said core being accommodated in said box, said front and rear legs elongating toward said box upper board;

a first air way formed in a bottom board of said box;

a blower attached to said first air way; and a second air way formed in a side board of said box, an air flow path defined between said first air way and said second air way through said core and said coil, wherein legs are downward disposed on said bottom board of said box, for placing said box under a state where said blower is separated from a floor to enable said box to function as a chair.

38. An air-cooling device for a coil in a urinary incontinence treatment device, to which pulse current or alternating current is supplied, to generate magnetic fluxes toward an area from a front of an urethral orifice to a rear of an anus for inducing eddy currents in a living body, comprising:

a box having an upper board which is electrically insulative and nonmagnetic;

a core having front and rear side legs, and a coil wound around said core, said core being accommodated in said box, said front and rear legs elongating toward said box upper board;

a first air way formed in a bottom board of said box;

a blower attached to said first air way;

a second air way formed in a side board of said box, an air flow path defined between said first air way and said second air way through said core and said coil;

a seat portion mounted on said box;

ducts respectively formed between said side boards and said side portions opposed to said side boards, said blower placed to said bottom board of said ducts;

cutout portions, communicating with said ducts, formed in side end portions of said seat portion, respectively; and ventilation cutout portions formed in intermediate regions in anteroposterior directions of said side portions and in side areas of said blower.

39. An air-cooling device for a coil in a urinary incontinence treatment device, to which pulse current or alternating current is supplied, to generate magnetic fluxes toward an area from a front of an urethral orifice to a rear of an anus for inducing eddy currents in a living body, comprising:

a box having an upper board which is electrically insulative and nonmagnetic;

a core having front and rear side legs, and a coil wound around said core, said core being accommodated in said box, said front and rear legs elongating toward said box upper board;

a first air way formed in a bottom board of said box;

a blower attached to said first air way; and a second air way formed in a side board of said box, an air flow path defined between said first air way and said second air way through said core and said coil, wherein said coil is defined by a pipe-shaped conductor member, ends of said conductor member are connected to a side face of said box, one of said ends is opened in air, and a blower is attached to another one of said ends.

* * * * *